(12) United States Patent
Zhao (10) Patent No.: US 9,610,450 B2
(45) Date of Patent: Apr. 4, 2017

(54) ANTENNA FOR AN IMPLANTABLE MEDICAL DEVICE

(75) Inventor: Yanzhu Zhao, Blaine, MN (US)

(73) Assignee: Medtronics, Inc., Minneapolis, MN (US)

( * ) Notice: Subject to any disclaimer, the term of this patent is extended or adjusted under 35 U.S.C. 154(b) by 1411 days.

(21) Appl. No.: 12/847,051

(22) Filed: Jul. 30, 2010

(65) Prior Publication Data

US 2012/0029323 A1 Feb. 2, 2012

(51) Int. Cl.
| | |
|---|---|
| *A61B 5/07* | (2006.01) |
| *A61B 5/02* | (2006.01) |
| *A61N 1/372* | (2006.01) |
| *A61B 5/00* | (2006.01) |
| *A61N 1/375* | (2006.01) |

(52) U.S. Cl.
CPC .......... *A61N 1/3727* (2013.01); *A61B 5/0031* (2013.01); *A61N 1/375* (2013.01); *A61N 1/37229* (2013.01)

(58) Field of Classification Search
CPC A61B 5/0031; A61N 1/37229; A61N 1/3727; G06K 7/10336
USPC .............. 600/300–302; 607/32, 60; 343/718, 343/866–873, 895, 896, 907–908
See application file for complete search history.

(56) References Cited

U.S. PATENT DOCUMENTS

| | | | |
|---|---|---|---|
| 2,324,462 A | 7/1943 | Leeds et al. | |
| 5,058,581 A | 10/1991 | Silvian | |
| 5,285,210 A | 2/1994 | Sato et al. | |
| 5,438,699 A | 8/1995 | Coveley | |
| 5,562,713 A * | 10/1996 | Silvian | ............................ 607/32 |
| 6,057,803 A | 5/2000 | Kane et al. | |
| 6,221,024 B1 | 4/2001 | Miesel | |

(Continued)

FOREIGN PATENT DOCUMENTS

| | | |
|---|---|---|
| EP | 1202775 B1 | 9/2006 |
| GB | 1439592 | 6/1976 |

(Continued)

OTHER PUBLICATIONS

Freudenthal, E.; Herrera, D.; Kautz, F.; Natividad, C.; Ogrey, A.; Sipla, J.; Sosa, A.; Betancourt, C.; Estevez, L., "Suitability of NFC for Medical Device Communication and Power Delivery," Engineering in Medicine and Biology Workshop, 2007 IEEE Dallas , vol., no., pp. 51,54, Nov. 11-12, 2007.*

(Continued)

*Primary Examiner* — Tiffany Weston (57) ABSTRACT

An antenna structure, for use in an implantable medical device, may include an inner portion that is magnetically coupled to an outer portion. In one example, the inner and outer portions include conductive loops. In accordance with the techniques of this disclosure, a capacitive sensor is electrically coupled to one of the conductive loops of the antenna of the implantable medical device. As the capacitance of the capacitive sensor changes as a function of the sensed parameter, an impedance of the antenna varies with the output of the capacitive sensor. This variation in impedance of the antenna modulates a carrier signal with the measured parameter. In other words, the measured parameter is modulated onto the carrier signal as a change in amplitude caused by variation in impedance of antenna during radiation/transmission.

16 Claims, 7 Drawing Sheets

(56) References Cited

U.S. PATENT DOCUMENTS

| | | |
|---|---|---|
| 6,295,473 B1* | 9/2001 | Rosar ............... 607/60 |
| 6,298,271 B1 | 10/2001 | Weijand |
| 6,418,004 B1 | 7/2002 | Mather et al. |
| 6,505,072 B1 | 1/2003 | Linder et al. |
| 6,561,975 B1 | 5/2003 | Pool et al. |
| 6,597,926 B1 | 7/2003 | Rek |
| 6,855,115 B2 | 2/2005 | Fonseca et al. |
| 6,993,297 B2 | 1/2006 | Smith, Jr. |
| 7,147,604 B1 | 12/2006 | Allen et al. |
| 7,245,117 B1 | 7/2007 | Joy et al. |
| 7,295,879 B2 | 11/2007 | Denker et al. |
| 7,432,723 B2 | 10/2008 | Ellis et al. |
| 7,439,723 B2 | 10/2008 | Allen et al. |
| 7,452,334 B2 | 11/2008 | Gianchandani et al. |
| 7,466,120 B2 | 12/2008 | Miller et al. |
| 7,481,771 B2 | 1/2009 | Fonseca et al. |
| 7,492,144 B2 | 2/2009 | Powers et al. |
| 7,498,799 B2 | 3/2009 | Allen et al. |
| 7,532,933 B2 | 5/2009 | Hastings et al. |
| 7,550,978 B2 | 6/2009 | Joy et al. |
| 7,574,792 B2 | 8/2009 | O'Brien et al. |
| 7,591,185 B1 | 9/2009 | Mothilal et al. |
| 7,595,647 B2 | 9/2009 | Kroh et al. |
| 7,618,363 B2 | 11/2009 | Yadav et al. |
| 7,621,036 B2 | 11/2009 | Cros et al. |
| 7,647,831 B2 | 1/2010 | Corcoran et al. |
| 7,647,836 B2 | 1/2010 | O'Brien et al. |
| 7,662,653 B2 | 2/2010 | O'Brien et al. |
| 7,667,547 B2 | 2/2010 | Ellis |
| 7,679,355 B2 | 3/2010 | Allen et al. |
| 7,699,059 B2 | 4/2010 | Fonseca et al. |
| 7,710,103 B2 | 5/2010 | Powers et al. |
| 7,748,277 B2 | 7/2010 | O'Brien et al. |
| 7,829,363 B2 | 11/2010 | You |
| 7,839,153 B2 | 11/2010 | Joy et al. |
| 7,854,172 B2 | 12/2010 | O'Brien et al. |
| 7,909,770 B2 | 3/2011 | Stern et al. |
| 7,932,732 B2 | 4/2011 | Ellis et al. |
| 7,936,174 B2 | 5/2011 | Ellis et al. |
| 7,966,886 B2 | 6/2011 | Corcoran et al. |
| 7,973,540 B2 | 7/2011 | Kroh et al. |
| 8,021,307 B2 | 9/2011 | White et al. |
| 8,026,729 B2 | 9/2011 | Kroh et al. |
| 8,118,749 B2 | 2/2012 | White et al. |
| 8,237,451 B2 | 8/2012 | Joy et al. |
| 8,353,841 B2 | 1/2013 | White et al. |
| 8,355,777 B2 | 1/2013 | White et al. |
| 8,360,984 B2 | 1/2013 | Yadav et al. |
| 8,412,352 B2 | 4/2013 | Griswold et al. |
| 8,515,559 B2 | 8/2013 | Roberts et al. |
| 8,669,770 B2 | 3/2014 | Cros |
| 8,805,505 B1 | 8/2014 | Roberts |
| 8,870,787 B2 | 10/2014 | Yadav et al. |
| 8,896,324 B2 | 11/2014 | Kroh et al. |
| 8,939,905 B2 | 1/2015 | Schugt et al. |
| 8,942,818 B2 | 1/2015 | Markowitz et al. |
| 8,983,619 B2 | 3/2015 | Cinbis et al. |
| 9,078,563 B2 | 7/2015 | Cros et al. |
| 2002/0003503 A1 | 1/2002 | Justice |
| 2002/0042637 A1 | 4/2002 | Stover |
| 2002/0147388 A1* | 10/2002 | Mass et al. ............... 600/300 |
| 2003/0105388 A1* | 6/2003 | Roy et al. ............... 600/300 |
| 2003/0112193 A1 | 6/2003 | Briggs |
| 2004/0122497 A1 | 6/2004 | Zhang et al. |
| 2004/0127161 A1 | 7/2004 | Leizerovich et al. |
| 2004/0147969 A1* | 7/2004 | Mann et al. ............... 607/17 |
| 2004/0183742 A1 | 9/2004 | Goff et al. |
| 2004/0212515 A1 | 10/2004 | Eaton et al. |
| 2005/0001779 A1 | 1/2005 | Copeland et al. |
| 2005/0065589 A1 | 3/2005 | Schneider et al. |
| 2005/0065592 A1 | 3/2005 | Holzer |
| 2005/0187482 A1 | 8/2005 | O'Brien et al. |
| 2005/0245840 A1 | 11/2005 | Christopherson et al. |
| 2005/0267550 A1 | 12/2005 | Hess et al. |
| 2005/0273014 A1* | 12/2005 | Gianchandani et al. ..... 600/505 |
| 2006/0161225 A1 | 7/2006 | Sormann et al. |
| 2006/0174712 A1 | 8/2006 | O'Brien et al. |
| 2006/0200031 A1 | 9/2006 | White et al. |
| 2007/0085755 A1* | 4/2007 | Webb et al. ............... 343/866 |
| 2007/0091006 A1 | 4/2007 | Thober et al. |
| 2007/0100385 A1 | 5/2007 | Rawat et al. |
| 2007/0208403 A1 | 9/2007 | Della Santina et al. |
| 2007/0229278 A1 | 10/2007 | Nagata et al. |
| 2007/0270934 A1 | 11/2007 | Stern et al. |
| 2007/0282210 A1 | 12/2007 | Stern |
| 2008/0046037 A1 | 2/2008 | Haubrich et al. |
| 2008/0080452 A1 | 4/2008 | Rofougaran |
| 2008/0081581 A1 | 4/2008 | Rofougaran |
| 2008/0081962 A1* | 4/2008 | Miller et al. ............... 600/301 |
| 2008/0097567 A1 | 4/2008 | Haldeman |
| 2008/0130194 A1 | 6/2008 | Gray et al. |
| 2008/0147135 A1 | 6/2008 | Hareland |
| 2008/0183247 A1 | 7/2008 | Harding |
| 2008/0204338 A1 | 8/2008 | Rofougaran |
| 2008/0215117 A1 | 9/2008 | Gross |
| 2008/0280570 A1 | 11/2008 | Blin |
| 2008/0288028 A1 | 11/2008 | Larson et al. |
| 2008/0300658 A1 | 12/2008 | Meskens |
| 2009/0005656 A1* | 1/2009 | Najafi et al. ............... 600/301 |
| 2009/0030291 A1 | 1/2009 | O'Brien et al. |
| 2009/0141592 A1* | 6/2009 | Huang ............... 367/181 |
| 2009/0149825 A1 | 6/2009 | Berland et al. |
| 2009/0228074 A1 | 9/2009 | Edgell et al. |
| 2009/0270742 A1 | 10/2009 | Wolinsky et al. |
| 2009/0270948 A1* | 10/2009 | Nghiem et al. ............... 607/60 |
| 2010/0023085 A1 | 1/2010 | Wu et al. |
| 2010/0044444 A1 | 2/2010 | Jain et al. |
| 2010/0106223 A1 | 4/2010 | Grevious et al. |
| 2010/0114206 A1 | 5/2010 | Kaemmerer et al. |
| 2010/0249888 A1 | 9/2010 | Glenn et al. |
| 2011/0001812 A1 | 1/2011 | Zhao et al. |
| 2011/0028852 A1 | 2/2011 | Alfoqaha |
| 2011/0111706 A1 | 5/2011 | Noel |
| 2011/0126034 A1 | 5/2011 | Siegel et al. |
| 2012/0001812 A1 | 1/2012 | Zhao et al. |
| 2012/0029598 A1 | 2/2012 | Zhao |
| 2012/0064006 A1 | 3/2012 | Yadav |
| 2012/0109258 A1 | 5/2012 | Cinbis et al. |
| 2013/0027186 A1 | 1/2013 | Cinbis et al. |
| 2013/0245469 A1 | 9/2013 | Yadav et al. |
| 2014/0084943 A1 | 3/2014 | Kroh et al. |
| 2014/0088994 A1 | 3/2014 | Kroh |
| 2014/0275861 A1 | 9/2014 | Kroh et al. |
| 2014/0288085 A1 | 9/2014 | Yadav |
| 2014/0288459 A1 | 9/2014 | Yadav et al. |
| 2014/0330143 A1 | 11/2014 | Kroh et al. |
| 2015/0096167 A1 | 4/2015 | Zhao et al. |
| 2015/0097734 A1 | 4/2015 | Zhao et al. |
| 2015/0133796 A1 | 5/2015 | Yadav |
| 2015/0214604 A1 | 7/2015 | Zhao et al. |

FOREIGN PATENT DOCUMENTS

| | | |
|---|---|---|
| WO | 0105467 A1 | 1/2001 |
| WO | 2004014456 A2 | 2/2004 |
| WO | 2005067817 A1 | 7/2005 |
| WO | 2005115541 A1 | 12/2005 |
| WO | 2008034077 A2 | 3/2008 |
| WO | 2009055579 A1 | 4/2009 |

OTHER PUBLICATIONS

U.S. Appl. No. 12/512,869, filed Jul. 30, 2009; "Implantable Pressure Sensor with Membrane Bridge"; Arshad A. Alfoqaha.

"Magnetic Loop With Capacitive Load for 30-10M"; http://www.qsl.net/hb9mtn/hb9mtn_adf_loop.html; Retrieved: May 12, 2010.

(PCT/US2011/045936) PCT Notification of Transmittal of the International Search Report and the Written Opinion of the International Searching Authority.

(PCT/US2011/045919) PCT Notification of Transmittal of the International Search Report and the Written Opinion of the International Searching Authority, Mailed Oct. 28, 2011, 12 pages.

(56) References Cited

OTHER PUBLICATIONS

Office Action from U.S. Appl. No. 12/847,043, dated Apr. 2, 2014, 12 pages.
Henry Ott Consultants, "Frequency—Wavelength Chart", Feb. 14, 2001, 2 pages.
Office Action from U.S. Appl. No. 13/191,857, dated Sep. 11, 2015, 20 pp.
Office Action from U.S. Appl. No. 13/191,857, dated May 7, 2015, 21 pp.
Response to Final Office Action dated May 7, 2015, from U.S. Appl. No. 13/191,857, filed Aug. 7, 2015, 11 pp.
Final Rejection from U.S. Appl. No. 12/847,043, dated Aug. 3, 2015, 6 pp.
Response to Office Action dated Sep. 11, 2015, from U.S. Appl. No. 13/191,857, filed Dec. 10, 2015, 6 pp.
Response to Office Action dated Aug. 8, 2015, from U.S. Appl. No. 12/847,043, filed Nov. 3, 2015, 2 pp.
Response to Final Office Action dated Mar. 22, 2016, from U.S. Appl. No. 13/191,857, filed May 20, 2016, 9 pp.
Advisory Action from U.S. Appl. No. 13/191,857, dated Jun. 16, 2016, 3 pp.
Notice of Appeal from U.S. Appl. No. 13/191,857, filed Jun. 22, 2016, 1 pp.
Pre-Appeal Brief Request for Review from U.S. Appl. No. 13/191,857, filed Jun. 22, 2016, 6 pp.
Final Office Action from U.S. Appl. No. 13/191,857, dated Mar. 22, 2016, 23 pp.
Examinees Answer to Appeal Brief from U.S. Appl. No. 13/191,857, dated Jan. 3, 2017, 13 pages.

* cited by examiner

ANTENNA FOR AN IMPLANTABLE MEDICAL DEVICE

TECHNICAL FIELD

The disclosure relates generally to implantable medical devices and, in particular, to antennas for implantable medical devices.

BACKGROUND

A wide variety of implantable medical devices (IMDs) that sense one or more parameters of a patient, deliver a therapy to the patient, or both have been clinically implanted or proposed for clinical implantation in patients. An IMD may deliver therapy to or monitor a physiological or biological condition with respect to a variety of organs, nerves, muscles, tissues or vasculatures of the patient, such as the heart, brain, stomach, spinal cord, pelvic floor, or the like. The therapy provided by the IMD may include electrical stimulation therapy, drug delivery therapy or the like.

The IMD may exchange communications with another device. The IMD may exchange communications with another device that is implanted, attached to (e.g., worn by) the patient or otherwise located near the patient, or remote from the patient. The information exchanged may be information related to a condition of the patient, such as physiological signals measured by one or more sensors, or information related to a therapy delivered to the patient. The IMD may also receive information from the other device, such as information that may be used to control or configure a therapy to be provided to the patient. The IMD and the body worn device may exchange information using any of a variety of communication techniques, including inductive telemetry, magnetic telemetry, radio frequency (RF) telemetry or the like.

SUMMARY

This disclosure describes an antenna for an implantable medical device for wirelessly communicating with another device. As one example, the implantable medical device may be an implantable sensor for continuously monitoring a pressure within a vasculature of the patient. However, the techniques described in this disclosure are applicable to any implantable medical device that senses any of a variety of parameters of the patient, provides a therapy to the patient or both.

An antenna of the implantable medical device may include an inner portion that is magnetically coupled to an outer portion. In one embodiment, the inner and outer portions comprise conductive loops. In accordance with the techniques of this disclosure, an output of a capacitive sensor is electrically coupled to one of the conductive loops of the antenna of the implantable medical device. As will be described in detail herein, the capacitance of the capacitive sensor varies as a function of the sensed parameter, which in turn results in a change in impedance of the antenna. This variation in impedance resulting from the sensed parameter modulates a carrier signal for transmission to another device. In particular, the variation in impedance of the antenna as a function of the output of the capacitive sensor changes the amount of power transferred from a signal generator to the antenna and therefore the amplitude of the transmitted signal. In this manner, the measured parameter is modulated onto the carrier signal as a change in amplitude caused by variation in impedance of antenna during radiation/transmission.

In one example, the disclosure is directed to an apparatus comprising a capacitive sensor having an output that changes as a function of a sensed parameter and an antenna electrically coupled to the output of the capacitive sensor. A characteristic of the antenna changes as a function of the output of the capacitive sensor. The apparatus further includes a signal generator that generates a carrier signal and provides the carrier signal to the antenna. The changes in the characteristic of the antenna modulate the carrier signal with the sensed parameter.

An antenna structure as described in this disclosure provides a number of advantages. For example, implantable medical device may be less complex as it may not require as many components, e.g., no modulator. As such, IMD 20 may be smaller and/or consume less power. Moreover, IMD 20 may not require as much memory because the sensor measurements are transmitted to another device instead of being stored within IMD 20. Additionally, the sensor may provide a further communication range, e.g., up to several meters. Other advantages may also be realized by the antenna structure described herein.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
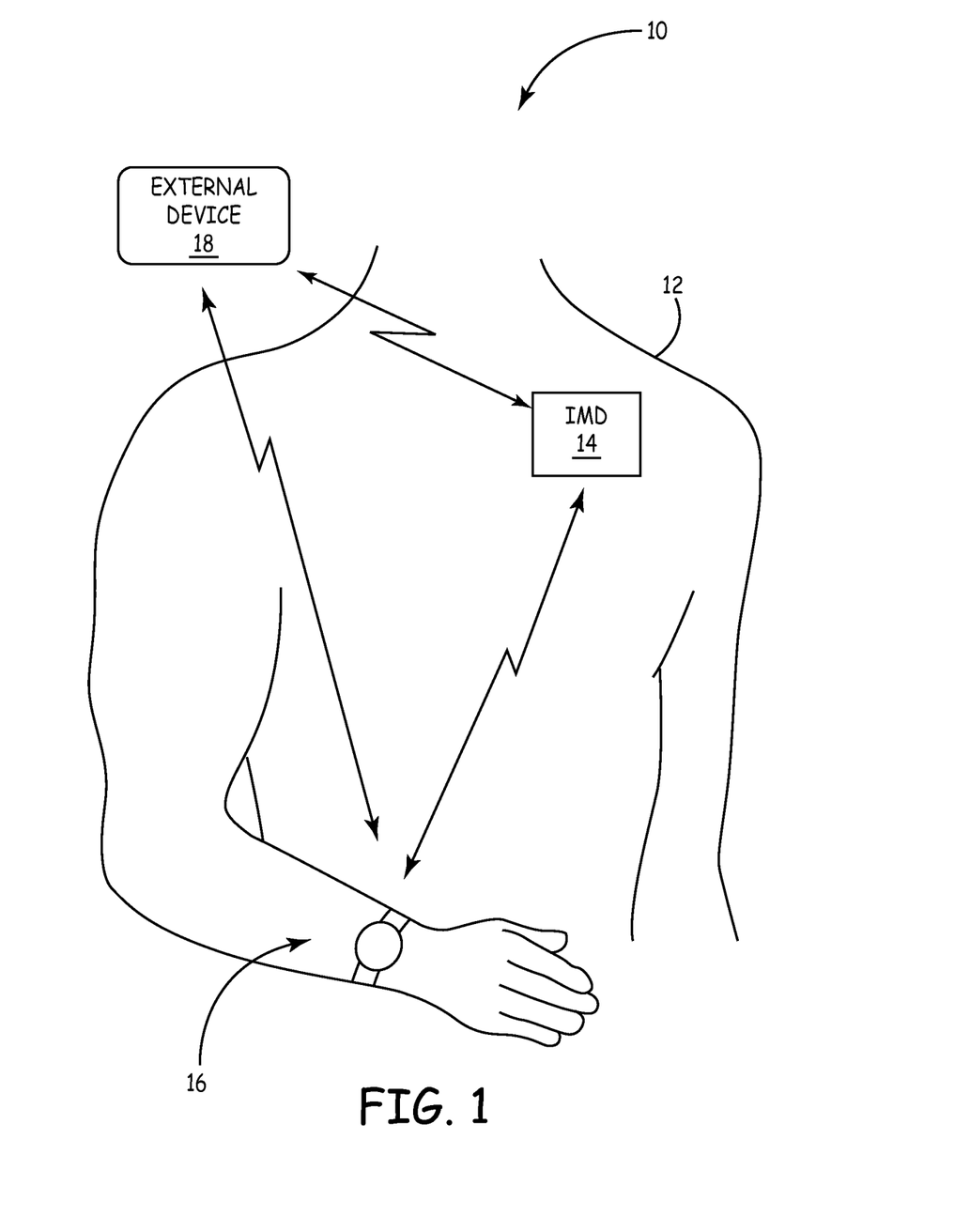
FIG. 1 is a conceptual diagram illustrating an example medical system.

FIG. 1 is a conceptual diagram illustrating an example medical system 10. Medical system 10 includes an implantable medical device (IMD) 14, a body worn device 16 and an external device 18. Medical system 10 may, however, include more of fewer implanted, body worn or external devices. IMD 14, body worn device 16 and external device 18 communicate with one another using any of a number of wireless communication techniques.

IMD 14 may be any of a variety of medical devices that sense one or more parameters of patient 12 and, in some instances, may also provide therapy to patient 12. In one example, IMD 14 may be a leadless IMD. In other words, IMD 14 is implanted at a targeted site with no leads extending from the IMD, thus avoiding limitations associated with lead-based devices. Instead, sensing and therapy delivery components are self-contained within IMD 14. In the case of a leadless sensor, IMD 14 includes one or more sensors that measure the parameter(s) of patient 12. In one example, IMD 14 may comprise an implantable pressure sensor placed within a vasculature or chamber of a heart of patient 12. Although this disclosure is described with respect to IMD 14 being an implantable pressure sensor implanted within a heart of patient 12, IMD 14 be placed in locations within patient 12, such as within or proximate to a spinal cord, brain, stomach, or pelvic floor, and may sense any of a variety of parameters, including heart activity, muscle activity, brain electrical activity, intravascular pressure, blood pressure, blood flow, acceleration, displacement, motion, respiration, or blood/tissue chemistry, such as oxygen saturation, carbon dioxide, pH, protein levels, enzyme levels or other parameter or combination of parameters.

In accordance with one aspect of this disclosure, the output of the sensor may change a characteristic of an antenna of IMD 14 to modulate a transmitted signal as a function of a sensed parameter. In one example, the sensor may be a capacitive sensor that is coupled to the antenna. In this case, an impedance of the antenna changes as a function of change in capacitance of the sensor caused by the measured parameter. The antenna therefore functions not only as a radiating structure to transmit communications, but also as a modulator. This may reduce the size and complexity of IMD 14 since there is no need for a separate modulator component.

Another device, such as body worn device 16, external device 18 or another IMD (not shown in FIG. 1), receives the signal transmitted by IMD 14, demodulates the signal to obtain the sensed parameter and stores the sensed parameter for later transmission or analysis. The other device may in turn monitor a condition of patient 12 or provide therapy to patient 12 as a function of the sensed parameters. In other instances, IMD 14 may provide the therapy to patient 12. IMD 14 may provide the therapy to patient 12 in accordance with a therapy program initially configured upon implantation or received from another device, such as another IMD, body worn device 16 or external device 18. As one example, IMD 14 may be a leadless cardiac IMD that provides electrical stimulation therapy (e.g., pacing, cardioversion, defibrillation, and/or cardiac resynchronization) to the heart of patient 12 via one or more electrodes. Although described above in the context of electrical stimulation therapy, IMD 14 may provide other therapies to patient 12, such as delivery of a drug or therapeutic agent to patient 12 to reduce or eliminate the condition of the patient and/or one or more symptoms of the condition of the patient, or provide no therapy at all.

Although IMD 14 is described above in the context of a leadless IMD, the techniques described in this disclosure may be utilized in the context of an IMD that is connected to one or more implantable leads (not shown) that include one or more electrodes for delivering therapy to patient 12. The leads may be implanted at the target tissue site, e.g., within one or more atria or ventricles of the heart, or within or proximate to the brain, stomach, pelvic floor, spine or the like.

Body worn device 16 communicates with IMD 14 via wireless communication. Body worn device 16 may receive the sensed parameters from IMD 14 and, in some instances, information related to therapies delivered to patient 12. Body worn device 16 may process the information from IMD 14 to monitor a condition of patient 12. In the case of an implantable pressure sensor, for example, body worn device 16 may receive pressure measurements from IMD 14 and process pressure measurements to monitor for cardiac condition, e.g., heart failure.

Body worn device 16 may alert patient 12 via an audible or visual alert when a cardiac condition is detected. Body worn device 16 may provide an alert to a care provider (e.g., physician) via a remote computing device and one or more networks. Body worn device 16 may relay the information received from IMD 14 to another IMD or to external device 18 for analysis. Body worn device 16 may also transmit information to IMD 14, such as information identifying the detected condition, information sensed by a sensor of body worn device 16 or another IMD implanted within patient 12, or information received from external device 16. The information transmitted to IMD 14 may, in some instances, control delivery of therapy by IMD 14.

Body worn device 16 is illustrated in FIG. 1 as being a watch. However, body worn device 16 may be any of a variety of body worn devices, such as a necklace, armband, belt, ring, bracelet, patch, or other device that is configured to be attached to, worn by, placed on or otherwise coupled to a body of patient 12. Alternatively, body worn device 16 may be a device placed in close proximity to or carried by patient 12, such as a cellular telephone, smart phone, pager, personal digital assistant (PDA), or other handheld computing device.

External device 18 may be a programming device or monitoring device that allows a user, e.g., physician, clinician or technician, to receive the sensed parameters from IMD 14 or body worn device 16 or to configure a therapy delivered by IMD 14. External device 18 may include a user interface that receives input from the user and/or displays the receive parameters to the user, thus allowing the user to analyze the data and/or program the therapy delivered by IMD 14. External device 18 may analyze the received parameters and display to the user an output of the analysis, such as a condition of a patient. External device 18 may be a dedicated hardware device with dedicated software for programming or otherwise communicating with IMD 14 and/or body worn device 16. Alternatively, external device 18 may be an off-the-shelf computing device running an application that enables external device 18 to program or otherwise communicate with IMD 14 and/or body worn device 16. In one example, external device 18 may be a computer workstation, such as a CareLink® monitor, available from Medtronic, Inc. of Minneapolis, Minn.

In some instances, IMD 14, body worn device 16 and external device 18 may be communicatively coupled with each other as well as other medical devices (not shown) to form a local area network, sometimes referred to as a body area network (BAN) or personal area network (PAN). Each device may therefore be enabled to communicate wirelessly along multiple pathways with each of the other networked devices. As such, IMD 14, body worn device 16 and external device 18 may represent a distributed system of devices that cooperate to monitor a condition of and/or provide therapy to patient 12. Additionally, one or more of the devices may be coupled to a remote computing device via one or more wired or wireless networks, such as a local area network (LAN), wide area network (WAN), or global network, such as the Internet.

IMD 14, body worn device 16 and external device 18 may communicate with one another by any of a number of wireless communication techniques. In some instances, IMD 14 may communicate with body worn device 16 or external device 18 via inductive telemetry. For example, a physician, technician or other user may place a telemetry head of external device 18, which includes an antenna, near IMD 14 and inductively communicate with IMD 14. In other instances, IMD 14 may communicate with body worn device 16 or external device 18 via RF telemetry. RF telemetry provides communication at further distances than the inductive telemetry such that no telemetry head is needed in the case of RF telemetry.

IMD 14, body worn device 16 and/or external device 18 may communicate in accordance with the Medical Implant Communications Service (MICS) band regulation and/or the Medical External Data Service (MEDS) frequency band regulation. The MICS band regulation defines communication requirements for the 402-405 MHz frequency band. In accordance with the MICS band regulations, the frequency band is divided into ten channels with each channel corresponding to a 300 kilohertz (kHz) sub-band. The MEDS band regulation defines a split channel band with a portion of the MEDS band occupying the 401-402 MHz frequency band and a portion of the MEDS band occupying the 405-406 MHz frequency band. The MEDS band is divided into 20 channels with each channel corresponding to a 100 kHz sub-band, with the first ten channels being located in the 401-402 MHz frequency band and the second ten channels being located in the 405-406 MHz frequency band. The devices of medical system 10 may, however, communicate using any frequency band regulation in addition to or instead of the MICS and MEDS band regulations, such as the industrial, scientific and medical (ISM) frequency bands.

Figure 2:
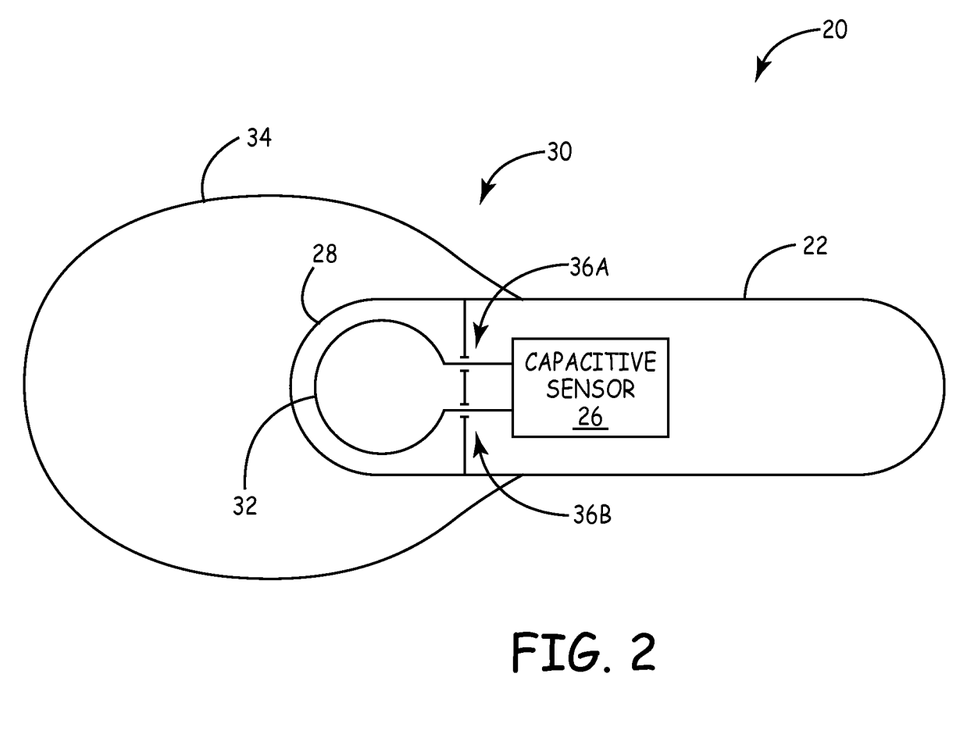
FIG. 2 is a schematic diagram illustrating an example implantable medical device.

FIG. 2 is a schematic diagram illustrating an example IMD 20 in further detail. IMD 20 may represent one example embodiment of IMD 14 of FIG. 1. IMD 20 includes a housing 22 that encloses components of IMD 20, including a capacitive sensor 26 and a carrier signal generator (not shown in FIG. 2). Housing 22 of IMD 20 has a long, thin cylindrical shape (e.g., a capsule-like shape) to accommodate delivery to and fixation within a vasculature of patient 12, such as within a pulmonary artery of a heart of patient 12. However, IMD 20 may be placed within or near other portions of the heart, such as in one of the chambers (atrial or ventricular), veins, vessels, arteries or other vasculature of the heart, such as the aorta, renal arteries, or inferior or superior vena cava. In further instances, IMD 20 may be placed on the outside of the heart or in locations other than the heart. Housing 22 may have a different shape depending on the location in which it will be implanted. Therefore, the techniques described in this disclosure should not be limited by the shape of housing 22 described herein.

Housing 22 may be formed of any of a variety of materials including conductive materials, non-conductive materials, or a combination thereof. Examples of a biocompatible, conductive material includes titanium, stainless steel, MP35N alloy (a nonmagnetic, nickel-cobalt-chromium-molybdenum alloy), platinum or the like. Examples of a biocompatible, non-conductive materials include silicone rubber, polyurethane, epoxy, acetyl co-polymer plastics, PolyEtherEtherKetone (PEEK), liquid crystal polymer (LCP) plastics, or the like. In one embodiment, housing 22 may include a header portion 28 made of a non-conductive material that includes at least a portion of an antenna 30 of implantable sensor 22. In this case, the remainder of housing 22 (besides header portion 28) may be made from a conductive material. In other embodiments, housing 22 is formed from a non-conductive material and no separate header portion 28 is necessary. Instead, the conductive loop 32 of antenna 30 may be located within housing 22.

Capacitive sensor 26 of IMD 20 measures a parameter associated with patient 12. In particular, the parameter associated with patient 12 causes a variation in capacitance of a capacitive element of capacitive sensor 26. As will be described in further detail, the output of capacitive sensor 26 may be electrically connected to a portion of antenna 30 such that variation in capacitance of capacitive sensor 26 changes an impedance of antenna 30 of IMD 20. The change in impedance of antenna 30 may be used to modulate the sensed parameters onto a carrier signal for transmission to another device, such as body worn device 16, external device 18 or another implantable medical device. Although described in the context of a capacitive sensor 26, the techniques of this disclosure may be utilized with other types of sensors having outputs that vary a characteristic of antenna 30 to modulate the sensed data onto a signal for transmission. In one example, capacitive sensor 26 may be a capacitive pressure sensor that changes capacitance in response to variations in pressure of a surrounding environment. In other instances, other types of sensors may be used that change other characteristics of antenna 30.

In one embodiment, antenna 30 includes an inner portion that is magnetically coupled to an outer portion. A conductive loop 32 within housing 22 may function as the inner portion of antenna 30 and a conductive loop 34 outside of housing 22 may function as the outer portion of antenna 30. As illustrated in FIG. 2, conductive loop 32 is smaller in size than conductive loop 34 and may be positioned such that it is at least partially within conductive loop 34. As such, throughout the remainder of this disclosure, conductive loop 32 within housing 22 is referred to as inner conductive loop 32 and conductive loop 34 located outside of housing 22 is referred to herein as outer conductive loop 34.

Outer conductive loop 34 (or at least a portion of outer conductive loop 34) is magnetically coupled to inner conductive loop 32. In other words, a change in current flow through inner conductive loop 32 generates a magnetic field that induces a current in outer conductive loop 34 thus coupling the energy to outer conductive loop 34. Likewise, a change in current flow through outer conductive loop 34 generates a magnetic field that induces a current in inner conductive loop 32 thus coupling the energy. In this manner, signals may be coupled to and from outer conductive loop 34 without any physical feed through or other direct electrical connection. If outer conductive loop 34 is electrically coupled to the signal generator (e.g., via feed throughs), forces created by pressure within the pulmonary artery or other environment within which IMD 20 is placed may result in mechanical strain at the point of the feed, possibly compromising the feed connection. Coupling energy to outer conductive loop 34 without feed throughs eliminates this potential problem.

In the example illustrated in FIG. 2, inner conductive loop 32 is positioned within the circumference of outer conductive loop 34. However, a portion or all of inner conductive loop 32 may be located outside of the circumference of outer conductive loop 34 as long as there is sufficient magnetic coupling between inner conductive loop 32 and outer conductive loop 34 to couple the signals between the two structures. Additionally, inner conductive loop 32 and outer conductive loop 34 may be coplanar or non-coplanar, coaxial or non-coaxial, collinear or non-collinear, or any combination thereof. Inner conductive loop 32 and outer conductive loop 34 may in one example be located in parallel planes, but not coplanar. In other embodiments, inner conductive loop 32 and outer conductive loop 34 may be located in different planes that are not parallel with one another, but are oriented such that there is sufficient magnetic coupling between inner conductive loop 32 and outer conductive loop 34.

Inner conductive loop 32 is electrically coupled to a telemetry module (not shown in FIG. 2). In the embodiments in which housing 22 includes a header portion 28, header portion 28 may include one or more electrical interconnects (such as feed ports 36A and 36B) that electrically connect inner conductive loop 32 of antenna 30 to the telemetry module within the other portion of housing 22. The telemetry module feeds signals to and receives signals from inner conductive loop 32 via feed ports 36.

In accordance with one aspect of this disclosure, the telemetry module feeds inner conductive loop 32 with an unmodulated carrier signal. The carrier signal may be, for example, a continuous wave signal generated by a signal generator (e.g., an oscillator). As described above, the change in capacitance of capacitive sensor 26 caused by the measured parameter (e.g., pressure) results in a change in impedance of inner conductive loop 32 and thus antenna 30 as a whole. This variation in impedance resulting from the sensed parameter modulates the carrier signal for transmission to another device, such as body worn device 16, external device 18 or another implantable medical device. In particular, the change in impedance of antenna 30 changes the amount of power transferred from the signal generator to antenna 30 and therefore the amplitude of the transmitted signal. In this manner, the measured parameter is modulated onto the carrier signal as a change in amplitude caused by variation in impedance of antenna 30 during radiation/transmission. The modulated carrier signal is magnetically coupled to outer conductive loop 34 and radiated to the other device. The function of the modulation can be determined by solving the equivalent circuit for the proposed antenna model. The model has the following critical parameters, such as the overall inductance from the loop, sensor capacitance, near field loss in tissue, and radiation resistance.

The structure of antenna 30 illustrated in FIG. 2 provides a number of advantages. As one example, implantable medical device may be less complex as it may not require as many components, e.g., no modulator. As such, IMD 20 may be smaller and/or consume less power. Moreover, IMD 20 may not require as much memory because the sensor measurements are transmitted to another device instead of being stored within IMD 20. Additionally, the coupling between inner conductive loop 32 and outer conductive loop 34 can be designed to achieve approximately an impedance match (e.g., 50 Ohms) at the feeding port, e.g., by changing a diameter of inner loop 32, a distance between the two loops, or the like, to achieve the best coupling.

In the example illustrated in FIG. 2, inner conductive loop 32 and outer conductive loop 34 have a circular shape and oval shape, respectively. However, inner conductive loop 32 and outer conductive loop 34 may be formed in any of a variety of shapes, including square, rectangle, triangle, oval or any other shape. In some instances, the size and shape of inner conductive loop 32 and outer conductive loop 34 may be dependent on a shape of header portion 28 and/or housing 22 of IMD 20, the location of implantation, the frequency at which communication occurs, or the like. In one example, In one example, inner conductive loop 32 can be a small fraction of the wavelength, such as less than or equal to approximately one-twentieth (1/20) of a wavelength at 400 MHz in human tissue (e.g., approximately 5 mm), and a circumference of outer conductive loop 34 may be from a fraction (e.g., approximately one-third (1/3)) to approximately one wavelength at 400 MHz in human tissue (e.g., approximately 3.2 cm to 9.6 cm).

IMD 20 may also include a fixation mechanism (not shown in FIG. 2) that affixes IMD 20 to the target location within patient 12. The fixation mechanism may be mechanically coupled to housing 22 via spot welding, adhesive or other coupling mechanism. The fixation mechanism may be any of a variety of fixation structures, including a generally tubular or cylindrical stent-like structure that is configured to lodge against a vessel wall, one or more tines, one or more loops, or other mechanism that exerts enough force against, embeds within, extends through or otherwise affixes IMD 20 to the target location. In one or more embodiments, at least a portion of the fixation mechanism may function as the outer portion of antenna 30, much the same as outer conductive loop 34. In other words, outer portion of antenna 30 may provide the dual function as a radiating portion of antenna 30 and as the fixation mechanism.

Figure 3:
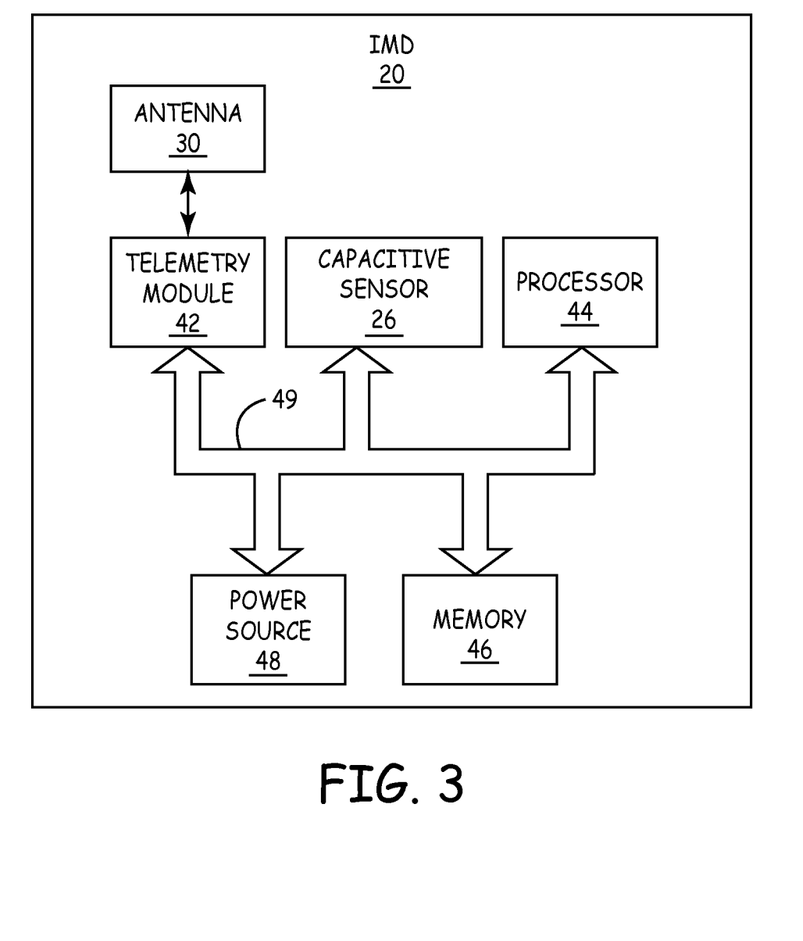
FIG. 3 is a block diagram illustrating components of the implantable medical device of FIG. 2 in further detail.

FIG. 3 is a block diagram illustrating components of IMD 20 of FIG. 2 in further detail. IMD 20 includes a capacitive sensor 26, antenna 30, telemetry module 42, processor 44, memory 46 and power source 48. The components of IMD 20 are shown to be interconnected by a data/communication bus 49, but may be interconnected by other means including direct electrical or non-electrical connections or a combination of different types of connections.

Capacitive sensor 26 measures one or more parameters of patient 12. Capacitive sensor 26 may, for example, be configured to measure pressure of the surrounding environment within which IMD 20 is placed. Although described with respect to capacitive sensor 26 measuring pressure, capacitive sensor 26 may measure other parameters, such as flow, acceleration, displacement, motion, or blood/tissue chemistry (e.g., oxygen saturation, carbon dioxide, pH, protein levels, or enzyme levels) or other parameter or combination of parameters.

The parameters measured by capacitive sensor 26 may be modulated onto a carrier signal in the manner described in this disclosure. In particular, the variation in capacitance of capacitive sensor 26 results in a change in impedance of antenna 30. This variation in impedance changes the amount of power that transferred from the signal generator (e.g., within telemetry module 42) to antenna 30 and therefore the amplitude of the transmitted signal. As a result, the change in impedance modulates the carrier signal from telemetry module 42 with the measured parameters.

Processor 44 may control telemetry module 42 to generate the unmodulated carrier signal for transmission. Processor 44 may control telemetry module 42 to intermittently (e.g., hourly, twice a day, daily, weekly, or the like) generate the unmodulated carrier signal. In this manner, processor 44 may control the time and/or duration at which IMD 20 transmits the sensor measurements. The measurements are only sent when the carrier signal is fed to antenna 30. When telemetry module 42 is not in the transmit mode, telemetry module 42 may be powered down (e.g., in the case of a transmit only IMD) or in a receive mode (e.g., in the case of an IMD with bi-directional communication). In the receive mode, IMD 20 receives communications from another medical device, such as body worn device 16, external device 18, or another implanted medical device. These inbound communications may control therapy delivery, change the frequency with which telemetry module 42 transmits the sensor measurements or the like.

As described in detail above, antenna 30 includes an inner portion (e.g., inner conductive loop 32) and an outer portion (e.g., outer conductive loop 34). Telemetry module 42 includes any suitable hardware, firmware, software or any combination thereof for communicating with another device. For example, telemetry module 42 may include appropriate signal generation, demodulation, frequency conversion, filtering, amplifier or other components for transmission and reception of data. Telemetry module 42 is also coupled to an antenna 30, such as any of the antenna configurations described herein, for transmitting and receiving signals.

Power source 48 may include a rechargeable or non-rechargeable battery. A non-rechargeable battery may be selected to last for several years, while a rechargeable battery may be charged from an external charging device on an as-need basis, e.g., daily or weekly basis. In either case, and especially in the case of the non-rechargeable battery, the amount of power of the battery is limited. As such, it is desirable to reduce the amount of power drained from power source 48 as much as possible.

IMD 20 of FIG. 3 is provided for purposes of illustration. IMD 20 may include more or fewer components than those illustrated in FIG. 3. For example, IMD 20 may also provide therapy, such as electrical stimulation therapy or drug delivery therapy, in accordance with parameters of one or more selected therapy programs. In this case, IMD 20 may include a therapy module (not shown) to generate therapy according to one or more therapy programs. In the case of electrical stimulation therapy, the therapy module may include a stimulation generator that generates and delivers electrical stimulation therapy, e.g., in the form of pulses or shocks, via one or more electrodes on housing 22, header 28 or a lead extending from the implantable medical device. Processor 44 may control the stimulation generator to deliver electrical stimulation pulses with amplitudes, pulse widths, frequency, and/or electrode polarities specified by the one or more therapy programs. In the case of drug delivery therapy, the therapy module may include a pump that delivers a drug or therapeutic agent, e.g., via a catheter or other delivery mechanism. Processor 44 may control the pump to deliver the drug or therapeutic agent with the dosage and frequency (or rate) specified by the one or more therapy programs. As such, the techniques of this disclosure should not be considered limited to the example described in FIG. 3.

Figure 4:
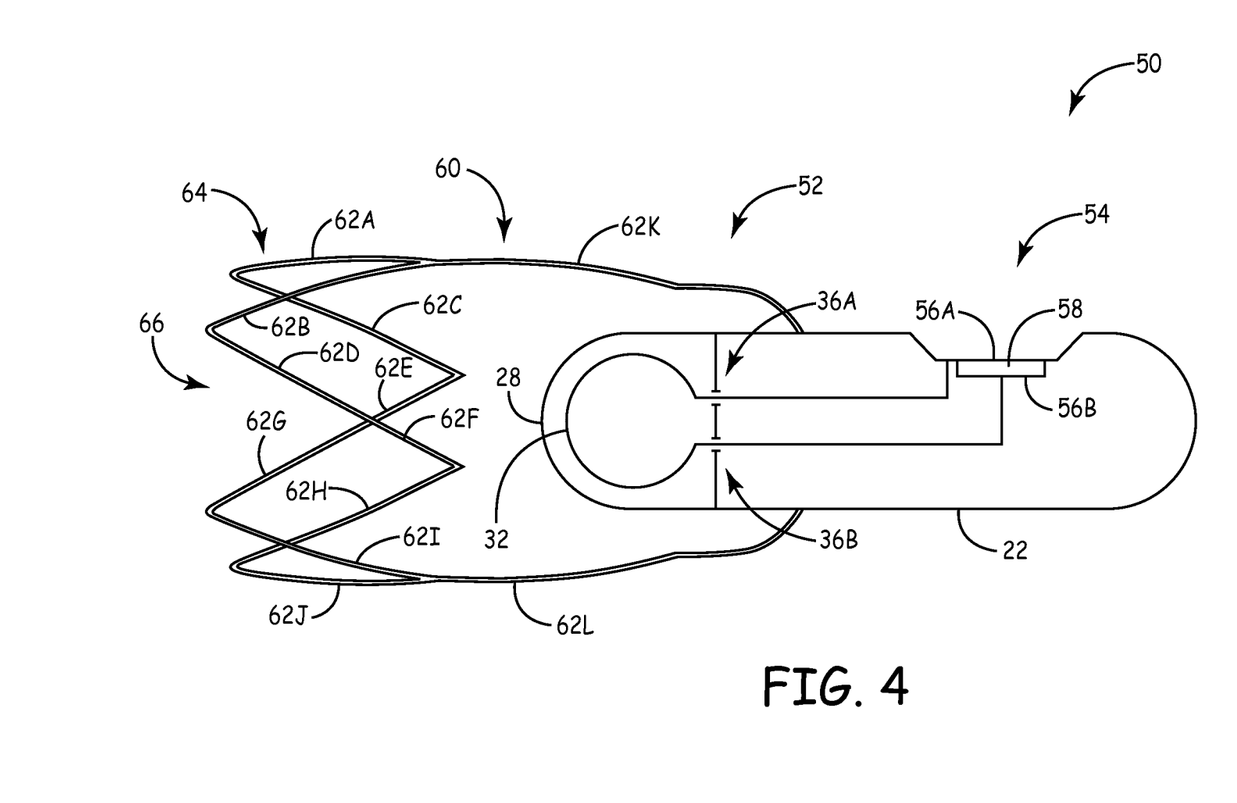
FIG. 4 is a block diagram illustrating another example implantable medical device that utilizes the aspects described in this disclosure.

FIG. 4 is a block diagram illustrating another example IMD 50 that utilizes the aspects described in this disclosure. IMD 50 may represent another example embodiment of IMD 14 of FIG. 1. IMD 50 includes an antenna 52 that includes an inner conductive loop 32 electrically coupled to a capacitive sensor, capacitive pressure sensor 54 in the example of FIG. 4.

Capacitive pressure sensor 54 includes a capacitor structure that includes a pair of capacitive plates 56A and 56B separated by a gap 58. Gap 58 may be filled with a dielectric, such as a solid, liquid or gas (including air). A first end of inner conductive loop 32 is connected to capacitive plate 56A and a second end of inner conductive loop 32 is connected to capacitive plate 56B. Capacitive plate 56A is a deformable diaphragm that is coated on an inner side with a thin layer of conductive material. Capacitive plate 56A deforms in response to pressure applied by the surrounding environment. In particular, the diaphragm flexes inwards in response to the applied pressure from the surrounding environment. As the diaphragm flexes inward, the distance between capacitive plates 56A and 56B decreases, causing a change in distance between capacitive plates 56A and 56B (i.e., size of gap 58) and thus a change in capacitance of pressure sensor 54.

Because the output of capacitive pressure sensor 54 is coupled to inner conductive loop 32 of antenna 52, the variation in capacitance of capacitive pressure sensor 54 results in a change in impedance of inner conductive loop 32 (and therefore antenna 52 as a whole). This variation in impedance of antenna 52 changes the amount of power that transferred from the signal generator of telemetry module 42 (or other component) to antenna 52 and therefore the amplitude of the transmitted signal. As a result, the change in impedance modulates the carrier signal from telemetry module 42 with the measured parameters. In other words, the impedance changes of the antenna affect the amplitude of the radiated signal as a function sensed pressure. The device receiving the signal transmitted by IMD 50 monitors the amplitude changes of the received signal and determines the pressure measurements as a function of the changes in amplitude. In this manner, the receiving device demodulates the signal to obtain the sensor measurements.

By way of example only and without limitation, capacitive pressure sensor 54 may comprise a pressure sensor constructed in a manner similar to that described in commonly assigned U.S. Pat. No. 6,221,024, entitled "Implantable Pressure Sensor and Method of Fabrication," U.S. patent application Ser. No. 12/512,869 filed Jul. 30, 2009 and entitled "Implantable Pressure Sensor with Membrane Bridge," and U.S. Pat. No. 7,591,185, entitled "Pressure Sensor Configurations for Implantable Medical Electrical Leads" the contents of each of which are hereby incorporated by reference for their description of pressure sensors. However, a pressure sensor may be constructed in any manner known in the art. Although described in the context of a capacitive pressure sensor 54, IMD 50 may include other types of capacitive sensors, such as a capacitive sensor for measuring acceleration, flow, mass, chemical composition or the like. Additionally, IMD 50 may include other types of sensors having outputs that vary a characteristic of antenna 52 to modulate the sensed data onto a signal for transmission.

In the example IMD 20 illustrated in FIG. 4, outer portion 60 of antenna 52 is a tubular or cylindrical stent-like structure. In this manner, the stent-like structure functions as the outer portion of antenna 52, much like outer loop 34 of antenna 30 of FIG. 2. Outer portion 60 may also function as a fixation mechanism that affixes IMD 50 to the target location, such as the wall of a vessel of patient 12. In one embodiment, outer portion 60 is mechanically coupled to housing 22 such that IMD 50 is substantially radially centered within vasculature when implanted. In other embodiments, outer portion 60 may be mechanically coupled to housing 22 such that IMD 50 is adjacent to the wall of the vasculature when implanted. Although illustrated as a stent-like structure, outer portion 60 of antenna 52 may be a structure that exerts enough force against, embeds within, extends through or otherwise affixes IMD 50 to the target location while still providing desirable radiating properties for antenna 52.

Outer portion 60 includes a plurality of struts 62A-62L that are arranged to form outer portion 60 of antenna 52. In particular, struts 62A-62J are arranged to form a ring 64 having a lumen 66. In the example illustrated in FIG. 4, struts 62A-62J form a zig-zag shaped ring 64. However, struts 62A-62J may be arranged to form a ring of a different shape, such as a sinusoidal shaped ring. Struts 62K and 62L mechanically couple on one end to ring 64 and on the opposite end to housing 22 to attach fixation mechanism 24 to housing 22.

Struts 62A-62L may be made from a variety conductive materials suitable for implantation, including, but not limited to, nickel-titanium (nitinol), stainless steel, tantalum, nickel, titanium, nickel-cobalt-chromium-molybdenum "superalloy," combinations of the above, and the like. In some embodiments, a portion of struts 62A-62L may be made of one or more the conductive materials described above while the other portions of struts 62A-62L may be made of non-conductive materials, such as polymeric materials. In this case, the conductive path of outer portion 66 may be specifically designed to obtain a particular radiation pattern. The material from which struts 62A-62L are made may be capable of being manipulated such that outer portion 60 may be radially compressed or otherwise manipulated to aid in delivery of IMD 50 to the target location. When located at the target location, outer portion 60 may be expanded in situ, e.g., via inflation of a balloon (not shown), such that at least a portion of struts 62 securely engage the vessel wall.

Outer portion 60 is illustrated in FIG. 4 as including a single ring 64, but outer portion 60 may include a plurality of rings joined in series to form the cylindrical tubular body of various lengths. The number of rings may depend upon the desired length of outer portion 60. For example when the target implantation site is relatively short, it would be desirable for outer portion 60 to have a smaller number of rings.

Outer portion 60 is located in close proximity to inner conductive loop 32 to achieve magnetic coupling needed to utilize the structure of outer portion 60 as a radiating element of antenna 52 in addition to serving as a fixation mechanism. In some embodiments, at least a portion of inner conductive loop 32 is located within lumen 66 defined by outer portion 60. The diameter of lumen 66 is greater than the diameter of housing 22 such that the portion of housing 22 enclosing inner conductive loop 32 may fit at least partially within lumen 66. In the example illustrated in FIG. 4, header portion 28 is located within the portion of lumen 66 defined by struts 62K and 62L. In other embodiments, more or less of housing 22 may be located within lumen 66. For example, header portion 28 of housing 22 may be located within the portion of lumen defined by ring 64 or additional rings connected in series with ring 64. Not only does disposing at least a portion of housing 22 within lumen 66 increase the magnetic coupling, the overall length of IMD 50 is reduced, which may be particularly advantageous when IMD 50 is implanted at an target site having a relatively short landing zone within the vessel.

Figure 5:
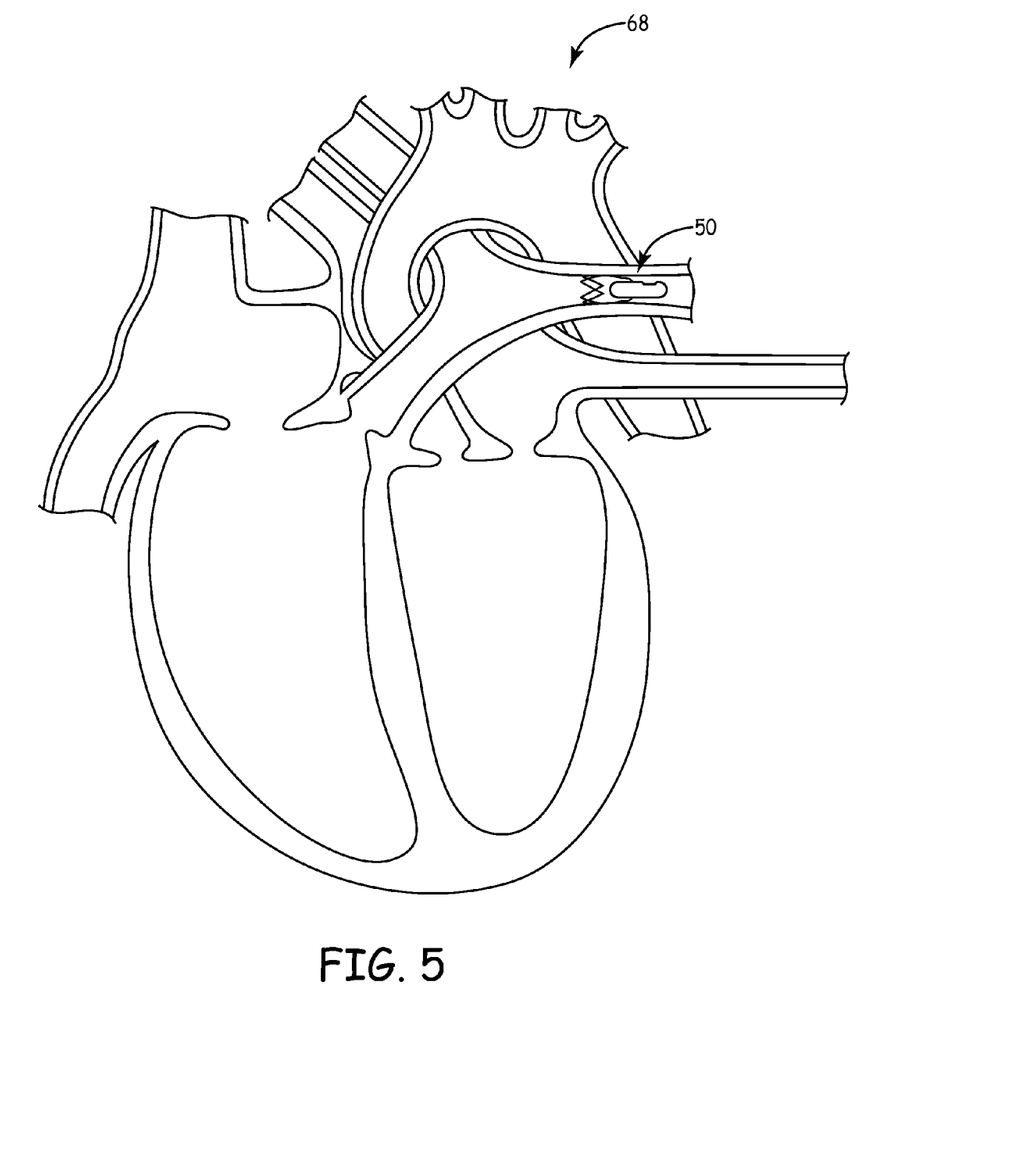
FIG. 5 is a schematic diagram illustrating implantable medical device of FIG. 4 implanted in a heart of a patient.

FIG. 5 is a schematic diagram illustrating IMD 50 of FIG. 4 implanted in a heart 68 of a patient 12. In the example illustrated in FIG. 5, IMD 50 is implanted in the pulmonary artery (PA) of heart 68 to sense pressure within the pulmonary artery. As such, IMD 50 may be sized to be delivered endoluminally using a delivery system tracked through the vasculature from a percutaneous entry site such as a femoral, jugular or subclavian vein or artery, and may have an outer diameter between 16-18 French (5.3-6 mm). However, IMD 50 may be placed within or near other portions of heart 68, such as in one of the chambers (atrial or ventricular), veins, vessels, arteries or other vasculature of heart 68, such as the aorta, renal arteries, or inferior or superior vena cava. In further instances, IMD 50 may be placed on the outside of heart 68 or in locations other than heart 68.

Figure 6:
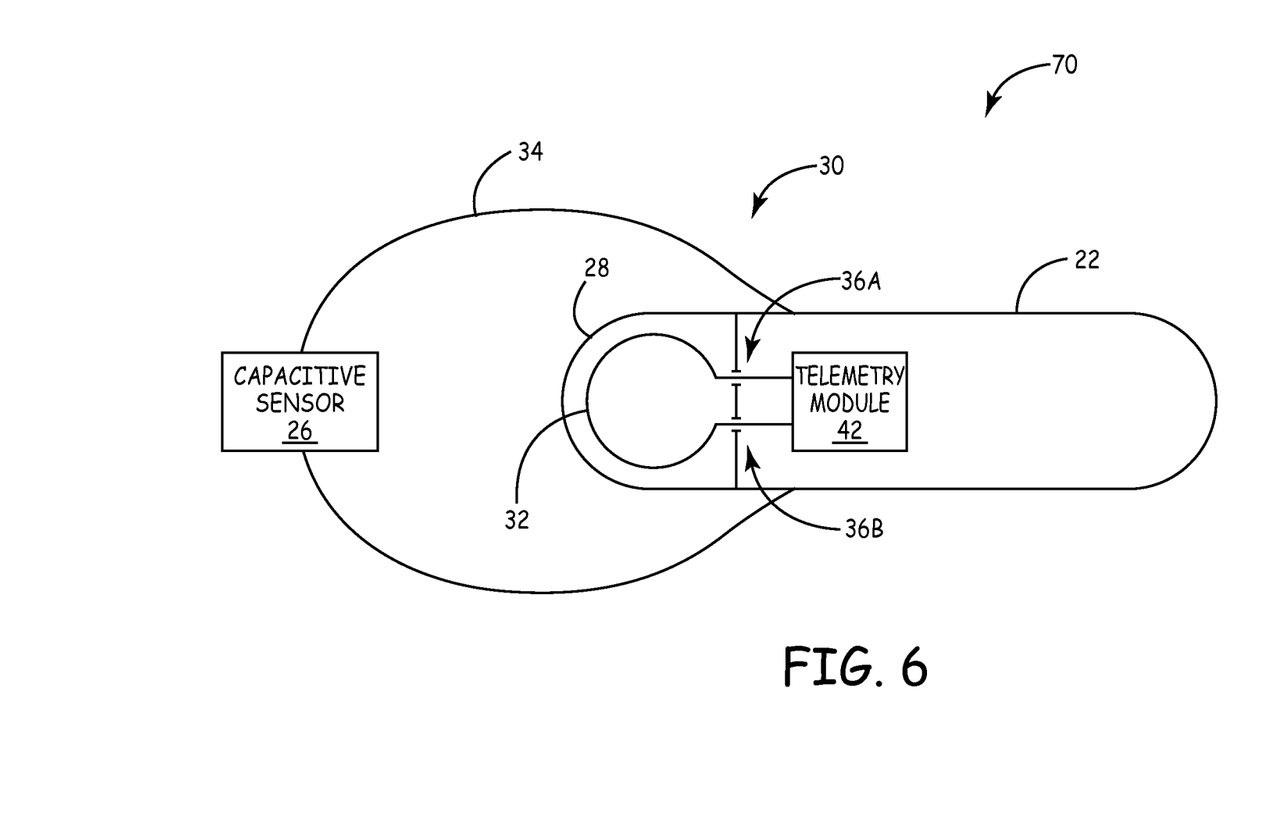
FIG. 6 is a schematic diagram illustrating another example implantable medical device in accordance with this disclosure.

FIG. 6 is a schematic diagram illustrating another example IMD 70 in accordance with this disclosure. IMD 70 is similar to IMD 20 of FIG. 2, but capacitive sensor 26 is electrically coupled to outer conductive loop 34 instead of inner conductive loop 32. In this case, capacitive sensor 26 may be located outside of housing 22. Alternatively, capacitive sensor 26 may be enclosed within housing 22 and electrically coupled to outer conductive loop 34 via one or more feed throughs extending through housing 22.

As described above, the change in capacitance of capacitive sensor 26 results in a change in impedance of outer conductive loop 34 and thus antenna 30 as a whole. This variation in impedance modulates the carrier signal coupled from inner conductive loop 32 with the measurements of the sensed parameter. In this manner, the measured parameter is modulated onto the carrier signal as the impedance of antenna 30 is modulated during radiation/transmission of the carrier signal. The modulated carrier signal is radiated to another device.

Figure 7:
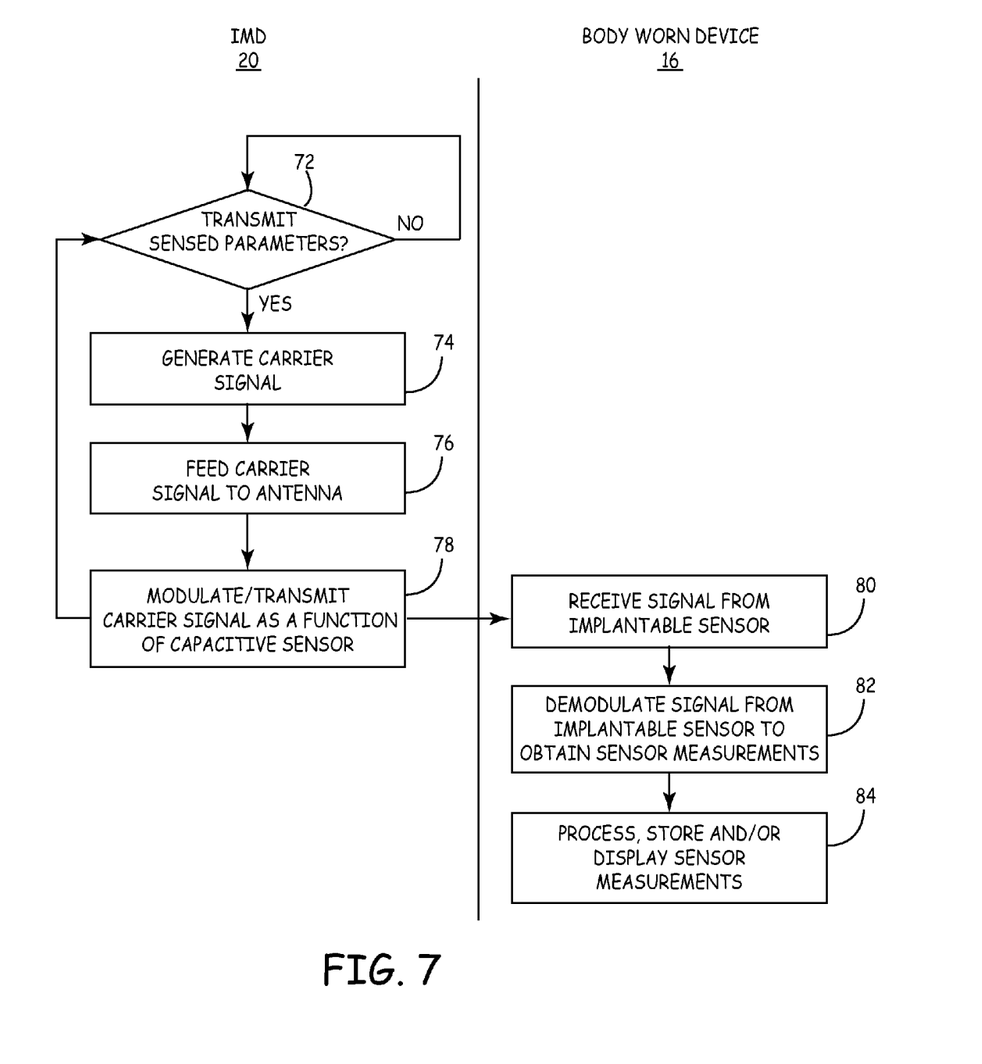
FIG. 7 is a flow diagram illustrating example operation on an implantable medical device in accordance with the techniques of this disclosure.

FIG. 7 is a flow diagram illustrating example operation on an IMD, such as any of IMDs 14, 20, 50 and 70, in accordance with the techniques of this disclosure. FIG. 7 will be described with reference to IMD 20 for exemplary purposes. Initially IMD 20 determines whether to transmit sensed parameters (72). Processor 44 may control IMD 20 to intermittently operate in a transmit mode to transmit the sensed parameters. Processor 44 may, for example, periodically configure IMD 20 into the transmit mode (e.g., hourly, daily or at some other interval) in accordance with a predefined schedule. Alternatively, processor 44 may control IMD 20 to enter the transmit mode in response to a signal or communication from another device (such as a wakeup signal). In yet another example, IMD 20 may be in a transmit mode all the time. The sensor modulated antenna method enables a much simplified device, e.g., less complex processor and memory.

When IMD 20 determines to transmit the sensed parameters ("YES" branch of block 72), the signal generator of IMD 20 generates a carrier signal (74). As described above, the carrier signal may be an unmodulated, continuous wave signal. The carrier signal is fed to antenna 30, which modulates and transmits the signal (76, 78). As described above, antenna 30 is connected to the capacitive sensor either at inner conductive loop 32 or outer conductive loop 34 (or other outer portion of the antenna in the other example embodiments). The variation in capacitance of capacitive sensor 26 due to the sensed parameter results in a change in impedance of antenna 30, which in turn changes the amount of power that transferred from the signal generator to antenna 30. As a result, the amplitude of the signal radiated by antenna 30 changes as the impedance of antenna 30 changes, thus modulating the carrier signal as a function of the parameter measurements.

Body worn device 16 receives the signal transmitted by IMD 20 (80). Body worn device 16 demodulates the signal to obtain the sensor measurements (82). For example, body worn device 16 monitors the amplitude changes of the received signal and determines the sensor measurements as a function of the changes in amplitude. In this manner, the receiving device demodulates the signal to obtain the sensor measurements. Body worn device 18 may process, store and/or display the sensor measurements (84).

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These examples, however, should not be considered limiting of the techniques described in this disclosure. For instance, the techniques of this disclosure may be used with outer conductive loops having different mechanical structures, including different "closed" loop structures and mechanical structures having open ends (or "open" loop structures). As another example, the inner loop may magnetically couple to portion of the housing of the implantable medical device thus using the implantable medical device housing as the outer conductive loop of the antenna. In yet another example, the inner loop may on a chip and magnetically couple to a planar loop around the chip. These and other examples are within the scope of the following claims.

The invention claimed is:

1. An implantable medical device (IMD) apparatus comprising:
   a capacitive sensor having an output that changes as a function of a sensed parameter;
   a housing that encloses one or more components of the IMD;
   an antenna electrically coupled to the output of the capacitive sensor, wherein an impedance of the antenna changes as a function of the output of the capacitive sensor, wherein the antenna comprises:
      a first portion having a conductive loop that is located within the housing, and
      a second portion including a conductive loop that is located outside the housing, wherein the second portion is magnetically coupled to the first portion to couple signals between the first portion and the second portion, and wherein the capacitive sensor is electrically connected to one of the first portion or the second portion; and
   a signal generator that generates a carrier signal and provides the carrier signal to the antenna, wherein the first portion of the antenna is electrically coupled to the signal generator and the changes in the impedance of the antenna modulates an amplitude of the carrier signal radiated by the antenna to another device with the sensed parameter.

2. The apparatus of claim 1, wherein the second portion of the antenna comprises a mechanical structure that affixes the apparatus to a target location.

3. The apparatus of claim 2, wherein the mechanical structure comprises a cylindrical structure that is configured to lodge against a vessel wall.

4. The apparatus of claim 1, wherein the capacitive sensor comprises one of a pressure sensor, a flow sensor and a chemical composition sensor.

5. The apparatus of claim 1, wherein the signal generator generates a continuous wave carrier signal.

6. The apparatus of claim 1, further comprising a processor that controls the signal generator to intermittently generate the carrier signal.

7. The apparatus of claim 1, further comprising a therapy delivery module that delivers a therapy to a patient.

8. The apparatus of claim 1, wherein the conductive loop of the first portion of the antenna is positioned at least partially within the second portion of the antenna.

9. The apparatus of claim 8, wherein the second portion of the antenna comprises a cylindrical structure configured to affix the apparatus to a target location and the conductive loop of the first portion of the antenna is positioned at least partially within the cylindrical structure.

10. The apparatus of claim 8, wherein the second portion of the antenna comprises a conductive loop and the conductive loop of the first portion of the antenna is positioned at least partially within a circumference of the conductive loop of the second portion of the antenna.

11. The apparatus of claim 10, wherein the conductive loop of the first portion of the antenna and the conductive loop of the second portion of the antenna are substantially coplanar.

12. An implantable medical device (IMD) apparatus comprising:
   a capacitive sensor having an output that changes as a function of a sensed parameter;
   an antenna having:
      a first portion having a conductive loop within a housing of the apparatus, wherein the housing encloses one or more components of the IMD, and
      a second portion including a conductive loop that is located outside of the housing of the apparatus, wherein the second portion is magnetically coupled to the first portion to couple signals between the first portion and the second portion, wherein the antenna is coupled to the output of the capacitive sensor; and
   a signal generator electrically coupled to first portion of the antenna to provide a carrier signal to the antenna;
   wherein an impedance of the antenna changes as a function of the output of the capacitive sensor to modulate an amplitude of the carrier signal with the sensed parameter during transmission of the carrier signal to another device.

13. The apparatus of claim 12, wherein the output of the capacitive sensor is electrically connected to the first portion of the antenna.

14. The apparatus of claim 12, wherein the output of the capacitive sensor is electrically connected to the second portion of the antenna.

15. The apparatus of claim 12, wherein the second portion of the antenna comprises a cylindrical structure configured to affix the apparatus to a target location and the conductive loop of the first portion of the antenna is positioned at least partially within the cylindrical structure.

16. The apparatus of claim 12, wherein the conductive loop of the first portion of the antenna is positioned at least partially within a circumference of the conductive loop of the second portion of the antenna.

* * * * *